United States Patent [19]
Ginns et al.

[11] Patent Number: 5,879,680
[45] Date of Patent: Mar. 9, 1999

[54] CLONED DNA FOR SYNTHESIZING UNIQUE GLUCOCEREBROSIDASE

[75] Inventors: Edward J. Ginns; Brian Martin, both of Bethesda; Kara A. Maysak, Chevy Chase, all of Md.; William K. Eliason, Reston, Va.; Mary E. LaMarca, Bethesda, Md.

[73] Assignee: The United States of America as represented by the Department of Health and Human Services, Washington, D.C.

[21] Appl. No.: 452,398

[22] Filed: May 26, 1995

Related U.S. Application Data

[62] Division of Ser. No. 186,256, Jan. 13, 1994, which is a continuation of Ser. No. 925,333, Aug. 6, 1992, abandoned, which is a continuation of Ser. No. 474,307, Feb. 5, 1990, abandoned, which is a continuation of Ser. No. 137,796, Dec. 23, 1987, abandoned.

[51] Int. Cl.$^6$ .......................... A61K 39/00; A61K 39/38; A61K 38/00; A61K 38/16
[52] U.S. Cl. ..................... 424/185.1; 424/94.61; 424/184.1; 514/2; 514/12; 514/14
[58] Field of Search ...................... 514/2, 12; 424/184.1, 424/94.61, 185.1

[56] References Cited

U.S. PATENT DOCUMENTS

| | | | |
|---|---|---|---|
| 3,910,822 | 10/1975 | Pentchev et al. | 195/62 |
| 4,386,026 | 5/1983 | Ponpipom et al. | 260/112.5 R |
| 4,745,051 | 5/1988 | Smith et al. | 435/68 |
| 5,236,838 | 8/1993 | Rasmussen et al. | 435/209 |

OTHER PUBLICATIONS

Choudary et al., "The Molecular Biology of Gaucher Disease and the Potential for Gene Therapy", Cold Spring Harbor Lab. (1986).
Dinur et al., *Proc. Natl. Acad. Sci. USA* 83: 1660–1664 (1986).
Sorge et al., *Proc. Natl. Acad. Sci. USA* 82: 7289–7293 (1985).
Tsuji et al., *The Journal of Biological Chemistry* 261: 50–53 (1986).
Takasaki et al., *The Journal of Biological Chemistry* 259: 10112–10117 (1984).
Furbish et al., *Proc. Natl. Acad. Sci. USA* 74: 3560–3563 (1977).
Basu et al., *The Journal of Biological Chemistry* 259: 1714–1719 (1984).
Erickson et al., *The Journal of Biological Chemistry* 260: 14319–14324 (1985).
Choudary et al., *Mol. Biol. Med.* 3: 293–299 (1986).
Sorge et al., *Proc. Natl. Acad. Sci. USA* 84: 906–909 (1987).
Sorge et al., *Proc. Natl. Acad. Sci. USA* 82: 5442–5445 (1985).
Beutler et al., *Proc. Natl. Acad. Sci. USA* 83: 7472–7474 (1986).
Grabowski et al., *Am. J. Hum. Genetics* pp. 499–510 (1985).
Ginns et al., *Biochem. Biophys. Res. Com.* 123: 574–580 (1984).
Reiner et al., *DNA* 6: 101–108 (1987).
Brady et al., *Birth Defects: Original Article Series* 16: 361–368 (1980).
Prabhakara et al., "Retrovirus–mediated Transfer of the Human Glucocerebrosidase Gene to Gaucher Fibroblasts", *Mol. Biol. Med.* 3: 293–299 (1986).
Grabowski et al., "Acid–glucosidase: Enzymology and Molecular Biology of Gaucher Disease", *Biochemistry and Molecular Biology*.
Tsuji et al., "A Mutation in the Human Glucocerebrosidase Gene in Neuronopathic Gaucher's Disease", *New England Journal of Medicine* 316: 570–575 (1987).
Tsuji et al., "Genetic Heterogeneity in Type 1 Gaucher Disease: Multiple Genotypes in Ashkenazic and Non–ashkenazic Individuals", *Proc. Natl. Acad. Sci. USA* 85: 2349–2352 (1988).
Smith et al., *Mol. and Cell. Biol.* 3(12): 2156–2165 (1983).
Luckow et al., *Bio/Technology* 6: 47–55 (1988).
Cameron et al., *TIBTECH* 7: 66–70 (1989).
Lebacq–Verheyden et al., *Mol. and Cell. Biol.* 8: 3129–3135 (1988).
Choudary et al. 1986 DNA 5,1:78.
Choudary et al. 1986a DNA 5,1:78.
Daebber et al. 1982. JBC. 257(5):2193–99.
Brady, 1983. In:Structural Carbohydrates in the Liver ed. Popper et al. pp. 497–505.
Takasaki et al. JBC 1984 259(16):10112–117.

*Primary Examiner*—Nita Minnifield
*Attorney, Agent, or Firm*—Needle & Rosenberg, P.C.

[57] ABSTRACT

The invention is directed to a pharmaceutical composition comprising a therapeutic amount of a glycosylated recombinantly-produced human glucocerebrosidase protein in a pharmaceutically acceptable carrier. The invention is further directed to a method of treating Gaucher's disease comprising administering to a subject afflicted with Gaucher's disease a therapeutic amount of a pharmaceutical composition comprising a therapeutic amount of a glycosylated recombinantly-produced human glucocerebrosidase protein in a pharmaceutically acceptable carrier.

2 Claims, 6 Drawing Sheets

FIG. 1-A

| | | | | | | | | | | | | | | | | | |
|---|---|---|---|---|---|---|---|---|---|---|---|---|---|---|---|---|---|
| 141 | Pro | Met | Ala | Ser | Cys | Asp | Phe | Ser | Ile | Arg | Thr | Tyr | Thr | Tyr | Ala | Asp | 156 |
| 479 | CCC | ATG | GCC | AGC | TGT | GAC | TTC | TCC | ATC | CGC | ACC | TAC | ACC | TAT | GCA | GAC | 526 |
| 157 | Thr | Pro | Asp | Asp | Phe | Gln | Leu | His | Asn | Phe | Ser | Leu | Pro | Glu | Glu | Asp | 172 |
| 527 | ACC | CCT | GAT | GAT | TTC | CAG | TTG | CAC | AAC | TTC | AGC | CTC | CCA | GAG | GAA | GAT | 574 |
| 173 | Thr | Lys | Leu | Lys | Ile | Pro | Leu | Ile | His | Arg | Ala | Leu | Gln | Leu | Ala | Gln | 188 |
| 575 | ACC | AAG | CTC | AAG | ATA | CCC | CTG | ATT | CAC | CGA | GCC | CTG | CAG | TTG | GCC | CAG | 622 |
| 189 | Arg | Pro | Val | Ser | Leu | Leu | Ala | Ser | Pro | Trp | Thr | Ser | Pro | Thr | Trp | Leu | 204 |
| 623 | CGT | CCC | GTT | TCA | CTC | CTT | GCC | AGC | CCC | TGG | ACA | TCA | CCC | ACT | TGG | CTC | 670 |
| 205 | Lys | Thr | Asn | Gly | Ala | Val | Asn | Gly | Lys | Gly | Ser | Leu | Lys | Gly | Gln | Pro | 220 |
| 671 | AAG | ACC | AAT | GGA | GCG | GTG | AAT | GGG | AAG | GGG | TCA | CTC | AAG | GGA | CAG | CCC | 718 |
| 221 | Gly | Asp | Ile | Tyr | His | Gln | Thr | Trp | Ala | Arg | Tyr | Phe | Val | Lys | Phe | Leu | 236 |
| 719 | GGA | GAC | ATC | TAC | CAC | CAG | ACC | TGG | GCC | AGA | TAC | TTT | GTG | AAG | TTC | CTG | 766 |
| 237 | Asp | Ala | Tyr | Ala | Glu | Pro | Phe | Leu | Gln | Phe | Trp | Ala | Val | Thr | Ala | Glu | 252 |
| 767 | GAT | GCC | TAT | GCT | GAG | CCT | TTC | TTA | CAG | TTC | TGG | GCA | GTG | ACA | GCT | GAA | 814 |
| 253 | Asn | Glu | Pro | Ser | Ala | Gly | Leu | Ser | Gly | Tyr | Pro | Phe | Gln | Cys | Leu | 268 |
| 815 | AAT | GAG | CCT | TCT | GCT | GGG | CTG | AGT | GGA | TAC | CCC | TTC | CAG | TGC | CTG | 862 |
| 269 | Gly | Phe | Thr | Pro | Glu | His | Gln | Arg | Asp | Phe | Ile | Ala | Arg | Asp | Leu | Gly | 284 |
| 863 | GGC | TTC | ACC | CCT | GAA | CAT | CAG | CGA | GAC | TTC | ATT | GCC | CGT | GAC | CTA | GGT | 910 |
| 285 | Pro | Thr | Leu | Ala | Asn | Ser | Thr | His | His | Asn | Val | Arg | Leu | Leu | Met | Leu | 300 |
| 911 | CCT | ACC | CTC | GCC | AAC | AGT | ACT | CAC | CAC | AAT | GTC | CGC | CTA | CTC | ATG | CTG | 958 |

FIG. 1-B

| | | | | | | | | | | | | | | | | | |
|---|---|---|---|---|---|---|---|---|---|---|---|---|---|---|---|---|---|
| 301<br>959 | Asp<br>GAT | Asp<br>GAC | Gln<br>CAA | Arg<br>CGC | Leu<br>TTG | Leu<br>CTG | Pro<br>CCC | His<br>CAC | Trp<br>TGG | Ala<br>GCA | Lys<br>AAG | Val<br>GTG | Val<br>GTA | Leu<br>CTG | Thr<br>ACA | | 316<br>1006 |
| 317<br>1007 | Asp<br>GAC | Pro<br>CCA | Glu<br>GAA | Ala<br>GCA | Ala<br>GCT | Lys<br>AAA | Tyr<br>TAT | Val<br>GTT | His<br>CAT | Gly<br>GGC | Ile<br>ATT | Ala<br>GCT | Val<br>GTA | His<br>CAT | Trp<br>TGG | Tyr<br>TAC | 332<br>1054 |
| 333<br>1055 | Leu<br>CTG | Asp<br>GAC | Phe<br>TTT | Leu<br>CTG | Ala<br>GCT | Pro<br>CCA | Ala<br>GCC | Lys<br>AAA | Phe<br>TTT | Leu<br>CTA | Thr<br>ACC | Leu<br>CTA | Gly<br>GGG | Glu<br>GAG | Thr<br>ACA | His<br>CAC | Arg<br>CGC | 348<br>1102 |
| 349<br>1103 | Leu<br>CTG | Phe<br>TTC | Pro<br>CCC | Asn<br>AAC | Thr<br>ACC | Met<br>ATG | Leu<br>CTC | Phe<br>TTT | Ala<br>GCC | Ser<br>TCA | Glu<br>GAG | Cys<br>TGT | Ala<br>GCC | Val<br>GTG | Gly<br>GGC | Ser<br>TCC | 364<br>1150 |
| 365<br>1151 | Lys<br>AAG | Phe<br>TTC | Glu<br>GAG | Ser<br>AGT | Val<br>GTG | Arg<br>CGG | Leu<br>CTA | Gly<br>GGC | Ser<br>TCC | Trp<br>TGG | Asp<br>GAT | Arg<br>CGA | Gly<br>GGG | Met<br>ATG | | 380<br>1198 |
| 381<br>1199 | Gln<br>CAG | Tyr<br>TAC | Ser<br>AGC | His<br>CAC | Ser<br>AGC | Ile<br>ATC | Ile<br>ATC | Thr<br>ACG | Asn<br>AAC | Leu<br>CTC | Leu<br>CTG | Tyr<br>TAC | His<br>CAT | Val<br>GTG | Val<br>GTC | Gly<br>GGC | 396<br>1246 |
| 397<br>1247 | Trp<br>TGG | Thr<br>ACC | Asp<br>GAC | Trp<br>TGG | Asn<br>AAC | Leu<br>CTT | Ala<br>GCC | Leu<br>CTG | Asn<br>AAC | Pro<br>CCC | Glu<br>GAA | Gly<br>GGA | Gly<br>GGA | Pro<br>CCC | Asn<br>AAT | Trp<br>TGG | 412<br>1294 |
| 413<br>1295 | Val<br>GTG | Arg<br>CGT | Asn<br>AAC | Phe<br>TTT | Val<br>GTC | Asp<br>GAC | Ser<br>AGT | Pro<br>CCC | Ile<br>ATC | Ile<br>ATT | Val<br>GTA | Asp<br>GAC | Ile<br>ATC | Thr<br>ACC | Lys<br>AAG | Asp<br>GAC | 428<br>1342 |

FIG. 1-C

```
429  Thr Phe Tyr Lys Gln Pro Met Phe Tyr His Leu Gly His Phe Ser Lys  444
1343 ACG TTT TAC AAA CAG CCC ATG TTC TAC CAC CTT GGC CAC TTC AGC AAG  1390

445  Phe Ile Pro Glu Gly Ser Gln Arg Val Gly Leu Val Ala Ser Gln Lys  460
1391 TTC ATT CCT GAG GGC TCC CAG AGA GTG GGG CTG GTT GCC AGT CAG AAG  1438

461  Asn Asp Leu Asp Ala Val Ala Leu Met His Pro Asp Gly Ser Ala Val  476
1439 AAC GAC CTG GAC GCA GTG GCA TTG ATG CAT CCC GAT GGC TCT GCT GTT  1486

477  Val Val Val Leu Asn Arg Ser Ser Lys Asp Val Pro Leu Thr Ile Lys  492
1487 GTG GTC GTG CTA AAC CGC TCC TCT AAG GAT GTG CCT CTT ACC ATC AAG  1534

493  Asp Pro Ala Val Gly Phe Leu Glu Thr Ile Ser Pro Gly Tyr Ser Ile  508
1535 GAT CCT GCT GTG GGC TTC CTG GAG ACA ATC TCA CCT GGC TAC TCC ATT  1582

509  His Thr Tyr Leu Trp Arg Arg Gln
1583 CAC ACC TAC CTG TGG CGT CGC CAG TGA TGG AGC AGA TAC TCA AGG AGG  1630

1631 CAC TGG GCT CAG CCT GGG CAT TAA AGG GAC A
```

FIG. 1-D

CLONED DNA FOR SYNTHESIZING UNIQUE GLUCOCEREBROSIDASE

This application is a division of application Ser. No. 08/186,256, filed Jan. 13, 1994 pending, which is a continuation of application Ser. No. 07/925,333, filed Aug. 6, 1992 now abandoned, which is a continuation of application Ser. No. 07/474,307, filed Feb. 5, 1990 now abandoned, which is a continuation of application Ser. No. 07/137,796, filed Dec. 23, 1987, now abandoned.

BACKGROUND OF THE INVENTION

Technical Field

The present invention is related to the construction of an expression vector for the synthesis of a recombinant enzyme. More particularly, the present invention is related to the large scale production of glucocerebrosidase by infecting invertebrate cells with a recombinant baculovirus containing the complete cDNA sequence for encoding glucocerebrosidase.

State of the Art

Mutation or deficiency of the lysosomal glycoprotein glucocerebrosidase (EC 3.2.1.45, β-D-glucosyl-N-acylsphingosine glycohydrolase) results in Gaucher's disease. It is estimated that there are about 20,000 cases of this genetic disease in the U.S. alone.

Published methods for producing large quantities of the active human enzyme involve purification of the protein from large amounts of human tissue, such as placenta. It should be noted, however, that the placental glucocerebrosidase has carbohydrate structure different than that of the enzyme found in human liver, spleen, brain or macrophages.

Construction of a cDNA clone containing the entire human glucocerebrosidase coding region has been known (Sorge et al, *Proc. Natl. Acad. Sci. USA* 82:7289–7293, 1985). However, as it will become clear vide infra, both the cDNA clone of the present invention and the enzyme synthesized therefrom, are qualitatively different from the similar prior art entities.

SUMMARY OF THE INVENTION

It is, therefore, an object of the present invention to provide an active clone of human cDNA containing the complete coding region for the lysosomal glycoprotein glucocerebrosidase (GCS), preferably introduced into the genome of *Autographa californica* nuclear polyhedrosis virus downstream to the polyhedrin promoter.

It is a further object of the present invention to provide synthetic, isolated and substantially pure recombinant GCS in which the carbohydrate moiety in the glycoprotein structure is different from the human placental GCS.

It is another object of the present invention to provide a method for large scale production of recombinant GCS by infecting *Spodoptera frugiperda* cells with the recombinant vector of the present invention.

It is a still further object of the present invention to provide a method for treating Gaucher's disease comprising administering to a subject inflicted with Gaucher's disease, therapeutic amount of the recombinant GCS to alleviate the disease condition.

Other objects and advantages of the present invention will become apparent from the following Detailed Description of the Invention.

BRIEF DESCRIPTION OF THE DRAWINGS

These and other objects, features and many of the attendant advantages of the invention will be better understood upon a reading of the following detailed description when considered in connection with the accompanying drawings wherein:

FIGS. 1-A to 1-D shows DNA sequence of a human glucocerebrosidase cDNA used for the construction of the baculovirus derived vector, pAC373/GC. In addition to the nucleotide sequence, the amino acids encoded by the coding sequence of the cDNA for human lysosomal glucocerebrosidase is also shown;

DETAILED DESCRIPTION OF THE INVENTION

Figure 1:
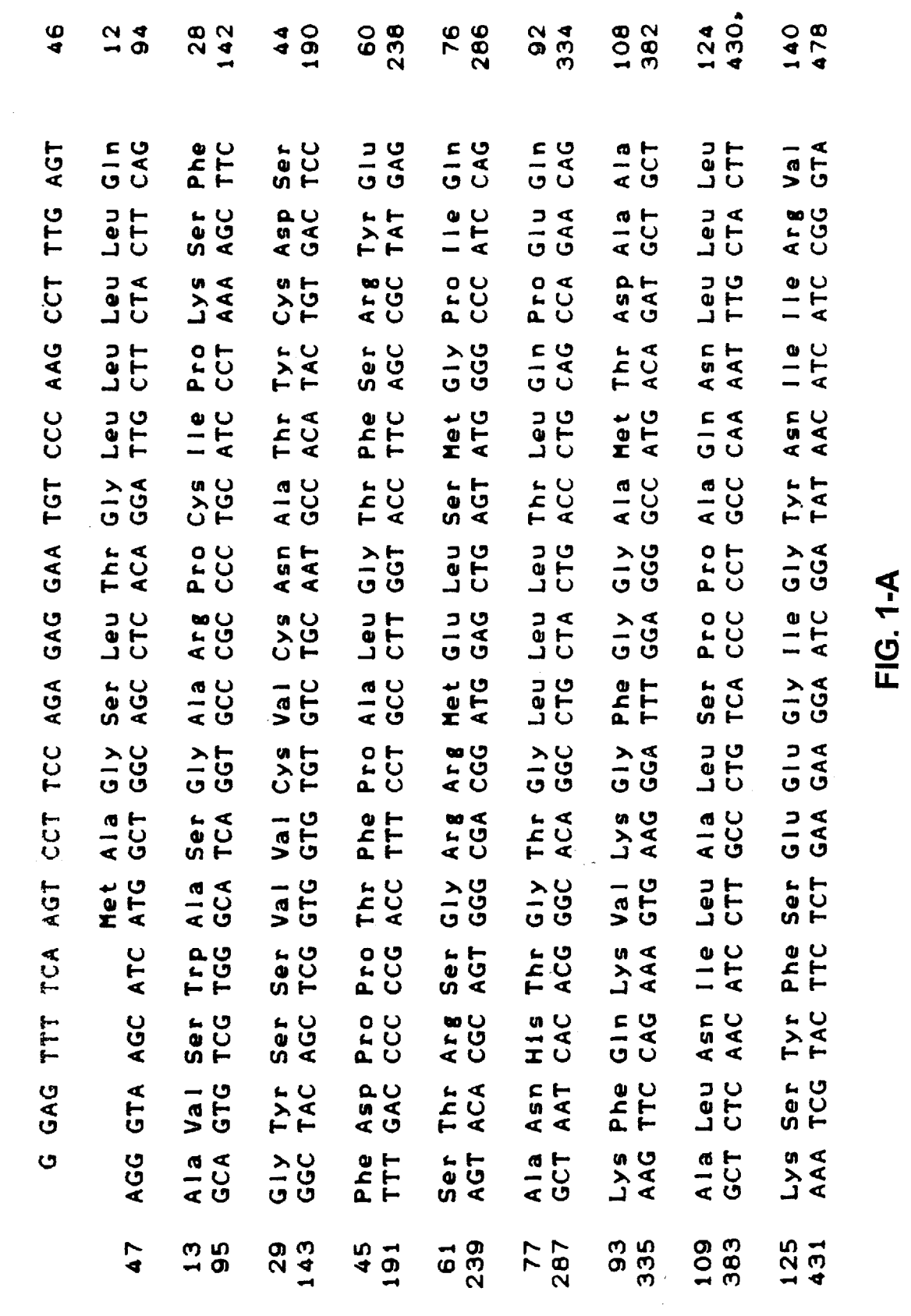
Figure 2:
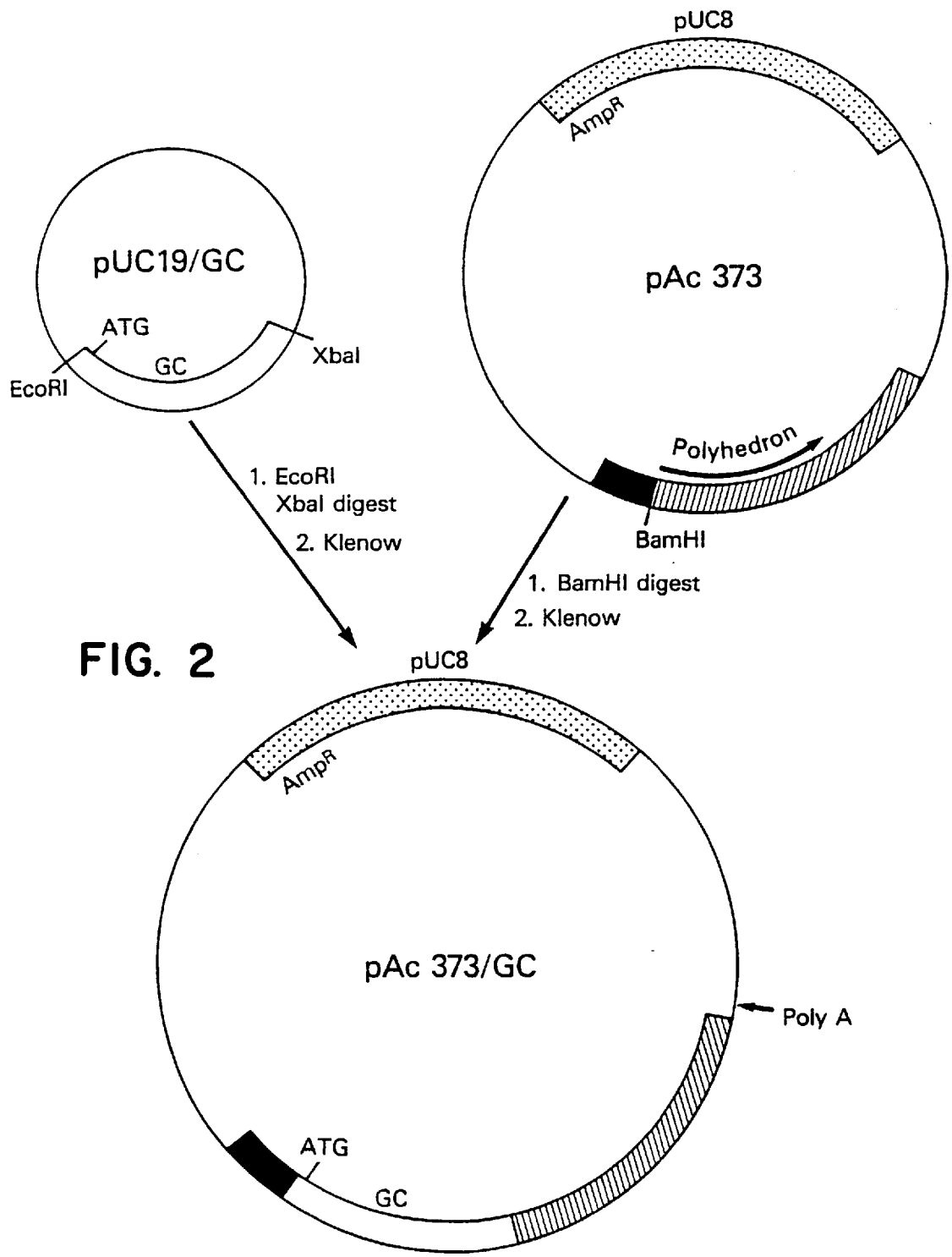
FIG. 2 shows schematic construction of baculovirus derived vector containing cDNA for human glucocerebrosidase. The cDNA for human glucocerebrosidase containing the sequence shown in FIG. 1 was blunted and then ligated into the SmaI site of a pUC vector (for instance pUC19) yielding pUC19/GC with the cDNA for human glucocerebrosidase lying between unique EcoRI and XbaI sites. The human glucocerebrosidase cDNA could be excised with EcoRI and XbaI, blunted, and ligated in a blunted BamHI site in the baculovirus derived vector, pAC373/GC. This baculovirus vector construct, pAC373/GC, contains human glucocerebrosidase cDNA downstream from the polyhedrin promotor in a 5' to 3' orientation.

The above and various other objects and advantages of the present invention are achieved by a cDNA clone containing the complete coding sequence for human lysosomal glucocerebrosidase as shown in FIG. 1-A to 1-D, said clone having been inserted into the genome of *Autographa californica* nuclear polyhedrosis virus downstream to the polyhedrin promoter as shown schematically in FIG. 2.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference.

The term "substantially pure" as defined herein means as pure as can be obtained by standard purification techniques known to one of ordinary skill in the art.

Materials and Methods

Materials:
Restriction endonucleases and recombinant enzymes were obtained from either Life Science Technologies or New England Biolabs. Concanavalin A-Sepharose was obtained from Pharmacia. Octyl-Agarose and Decyl-Agarose were purchased from ICN Biomedicals, Inc. Polyvinylidene difluoride (PVDF) membranes, 0.45 μm pore size, were obtained from Millipore Corp. Sequencer chemicals and solvents for on-line PTH analysis were purchased from Applied Biosystems Inc. Endoglycosidase H was from Miles Scientific while N-Glycanase was purchased from Genzyme Corp.

Construction of recombinant Baculoviruses:

Spodoptera frugiperda SF9 cells, plasmid pAc373, and wild-type AcNPV strain E2 were obtained from Max Summers, Texas A&M University. The SF9 cells were maintained in culture at 28° C. using TNM-FH media (GIBCO) (Hink, *Nature* 226:466, 1970). The cDNA for human glucocerebrosidase was obtained from plasmid pUC19/GC, a derivative of an Okayama-Berg clone from a SV40 transformed human fibroblast cDNA library (Okayama et al, *Mol. Cell Biol.* 3:280, 1983). This cDNA contained 5' and 3' untranslated sequences as well as the complete coding region for glucocerebrosidase. As shown in FIG. 2, pAc373/GC was generated by ligation of the blunted EcoRI-XbaI fragment from pUC19/GC into the blunted unique BamHI site of pAC373. Correct orientation of the inserted glucocerebrosidase cDNA was determined by restriction endonuclease analysis.

Recombinant baculovirus containing the human glucocerebrosidase coding sequence under transcriptional control of the polyhedrin promoter was produced by cotransfection of wild-type virus, AcNPV, with plasmid pAc373/GC into SF9 cells as described by Summers et al, (*Tex. Agric. Exp. Stn. Bull.* No. 1555, 1987). Five to six days after cotransfection, virus was harvested from the culture supernatant and used to inoculate new monolayers of SF9 cells in petri dishes that were subsequently overlaid with 1% low melting agarose containing TNM-FH medium. Seventy-two hours later the agarose overlay was removed and stored at 4° C., and the cell monolayer was blotted onto a nitrocellulose disk (BA85, Schleicher & Schuell). The disk was hybridized to the random primed, $^{32}P$ labelled EcoRI-XbaI glucocerebrosidase cDNA fragment from pUC19/GC. Areas on the agarose overlay corresponding to points on the nitrocellulose disk showing hybridization signal were excised and placed in one milliliter of TNM-FH medium. This virus was used for infection of SF9 monolayer cultures and an additional 5 cycles of infection-hybridization were carried out during the plaque purification procedure.

A deposit of PAc373/GC has been made at the ATCC, Rockville, Md. on Nov. 30, 1987 under the accession number 40393. The deposit shall be viably maintained, replacing if it became non-viable, for a period of 30 years from the date of the deposit, or for 5 years from the last date of request for a sample of the deposit, whichever is longer, and made available to the public without restriction in accordance with the provisions of the law. The Commissioner of Patents and Trademarks, upon request, shall have access to the deposit.

Enzyme purification:

Recombinantly produced glucocerebrosidase was isolated using a modification of the procedure described by Furbish et al, (*Proc. Natl. Acad. Sci. USA* 74:3560, 1977). Cell culture supernatants were precipitated with 195 gm/liter ammonium sulfate. SF9 cell pellets containing the recombinantly produced glucocerebrosidase were extracted into 20 milliliters of sodium phosphate buffer, pH 6.5, containing 150 mM NaCl and 0.1% Triton X-100, followed by sonication twice at 50 W for 10 seconds. After precipitation with ammonium sulfate (195 gm/liter) the resuspended pellets were extracted with n-butanol, but ultrafiltration using a YM30 membrane (Amicon) replaced dialysis. After decyl-agarose and octyl-agarose hydrophobic interaction chromatrography at room temperature (about 22°–25° C.), the fractions containing glucocerebrosidase activity were pooled, and the ethylene glycol concentration reduced using an Amicon ultrafiltration cell fitted with a YM30 membrane.

Substantially pure enzyme is then obtained following standard conventional purification techniques well known in the art.

Carbohydrate characterization.

Endoglycosidase-H was dissolved in 100 mM sodium acetate, pH 6.0, at a final concentration of 10 units/ml. N-glycanase was supplied as a 250 unit/ml suspension in 50% glycerol. Either human placental enzyme or fifty microliter aliquot of decyl-agarose fraction containing glucocerebrosidase activity were adjusted to 0.5% NaDodSo$_4$/1M β-mercaptoethanol and boiled for two minutes. The samples were then diluted with appropriate buffer to either 200 mM sodium acetate, pH 6.0 (for endoglycosidase-H) or 200 mM sodium phosphate, pH 8.5 (for N-glycanase) to a final composition of 0.1% SDS, 0.7% NP-40, and 0.02M β-mercaptoethanol. The samples were again boiled for 1 min and then either endoglycosidase-H or N-glycanase added to final concentrations of 50 mu/ml or 20 Ul/ml, respectively. Digestions were for about 16 hours at 37° C. Carboxypeptidase Y was used as a control for both deglycosylation reactions.

Western blot analysis:

NaDodSO$_4$ polyacrylamide gel electrophoresis and Western blot analysis were performed as described by Ginns et al, (*Proc. Natl. Acad. Sci. USA* 79:5607, 1982).

Amino acid sequence analysis:

Samples used for amino acid sequence analysis were electrophoretically fractionated on NaDodSO$_4$ polyacrylamide gels as described above and then transferred to PVDF membranes as described by Matsudaira (*J.B.C.* 262:10035, 1987). Typically, after electrophoresis the gel was incubated in transfer buffer (0.1M CAPS, 10% methanol, pH 11.0) for 10 minutes prior to transblotting (50 ma for 4 hours). The gel was then washed with HPLC grade water for 5 minutes, stained with 0.1% Coomassie Blue R250 (in 50% methanol) for 5 minutes, and finally destained for 10 minutes with 50% methanol-10% acetic acid. The PVDF membrane was again washed with HPLC grade water, dried under a stream of nitrogen and stored in a sealing bag at −20° C. until used for amino acid sequencing.

Amino acid sequence analysis was accomplished using an Applied Biosystems Model 470A gas-phase sequencer equipped with a Model 120A on-line PTH-amino acid analyzer. The program 03R PTH was used directly for sequencing without pretreatment of the membrane strip with polybrene. An approximately 2×8 mm piece of PVDF membrane containing the protein band of interest was excised, centered on the teflon seal, and placed in the cartridge block of the sequencer. Multiple strips of the PVDF membrane could be stacked in this manner, thus increasing the amount of protein available for sequencing. The initial and repetitive yields for sequencing recombinant glucocerebrosidase were calculated by comparison with the yields obtained after 100 picomoles of human placenta glucocerebrosidase were electrophoresed, transblotted to PVDF and subjected to ten cycles of amino acid sequence (Table 1).

Table 1 compares the N-terminal amino acid sequence of mature human placental glucocerebrosidase to N-terminal amino acid sequence of recombinant human glucocerebrosidase using the methods described in the text. The N-terminal amino acids determined by direct chemical sequencing of the mature human placental and recombinant glucocerebrosidase are identical indicating that the signal sequence in the recombinantly produced enzymes are correctly processed. The blank in amino acid position 4 of the recombinant enzyme sequence is consistent with cysteine because cysteine was only identified in the placental enzyme following reduction and alkylation of the protein. The vertical arrow above the human cDNA sequence indicates the site of peptidase cleavage of the signal sequence.

(5) Several biochemical parameters of the human placental enzyme are different than that of the recombinant glucocerebrosidase produced by employing the baculovirus expression system:

1) The human placental enzyme on Western blot analysis showed a major band of cross reactive material (CRM) at 65 kDa, while the recombinantly produced enzyme has multile CRM forms between 67 and 52 kDa.

TABLE 1

| ATG | GCT | GGC | ... | TCA | GGT↓ | GCC | CGC | CCC | TGC | ATC | CCT | AAA | AGC | TTC | GGC | :cDNA |
|-----|-----|-----|-----|-----|------|-----|-----|-----|-----|-----|-----|-----|-----|-----|-----|-------|
| M   | A   | G   |     | S   | G    | A   | R   | P   | C   | I   | P   | K   | S   | F   | G   |       |
|     |     |     |     |     |      | A   | R   | P   | C   | I   | P   | K   | S   | F   | G   | :placental enzyme |
|     |     |     |     |     |      | A   | R   | P   | —   | I   | P   | K   | S   | F   | G   | :culture media |
|     |     |     |     |     |      | A   | R   | P   | —   | I   | P   | K   | S   | F   | G   | :SF9 cell pellet |

Glucocerebrosidase assays:

For pH profile and inhibition studies, glucocerebrosidase activity was measured using 100 mM potassium phosphate buffer containing 0.15% Triton X-100, 2.5 µl of β-D-[1-$^{14}$C] glucocerebroside (7.5 mg/ml in sodium taurocholate at 50 mg/ml), and the sample in the total volume of 200 ul. Preincubations with conduritol-B-epoxide were for 30 min at 37° C. For Km determination, β-glucosidase activity was assayed at pH 5.9 using the artificial substrate 4-methylumbellifery-β-D-glucopyranoside (4MUGP) in 100 mM potassium phosphate buffer containing 0.15% Triton X-100 and 0.125% sodium taurocholate. Purification of recombinant glucocerebrosidase was also monitored using 4MUGP.

FIGS. 1-A to 3 and Table 1 show the comparative results demonstrating the distinctive nature and properties of the cDNA clone and GCS of the present invention relative to the other known similar clones and enzymes, particularly comparing Sorge et al clone and placenta enzyme.

The distinctive properties are listed below:

(1) The human cDNA of the present invention for glucocerebrosidase differs in both nucleotide sequence and translated amino acid sequence from that of Sorge et al (PNAS, 1985, and Correction PNAS, 1986). Specifically, the cDNA of the present invention encodes for Leu (at 489) and Arg (at 514) while that of Sorge et al, encodes Pro and His at position 489 and 514, respectively. In addition, this cDNA sequence differs in three nucleotides from that reported by Tsuji et al, (J.B.C. 261:50, 1986).

(2) The high level baculovirus expression system differs from other expression systems as should be known to those familar with the subject. For example, the proteins expressed using bacterial hosts do not have the carbohydrate moieties that are added by eukaryotic hosts. Transient expresion systems utilizing COS cells or L cells produce only about 200,000 Units glucocerebrosidase/liter (Choudary et al, 1986) while the Baculovirus expression system produces over 2,400,000 units glucocerebrosidase/liter after three days of culture. Similarly, enzyme produced in heterologous cells following retroviral gene transfer produces approximately 200,000 units glucocerebrosidase/liter (Choudary et al, 1986, Cold Spring Harbor Symposia, Vol LI: 1047).

(3) The purification of human glucocerebrosidase from large amounts of human placenta must take into account the risk of the possible presence of infectious agents (such as but not limited to AIDS virus and hepatitis virus). The recombinantly produced glucocerebrosidase is not associated with these potential complications.

(4) The carbohydrate structure of glucocerebrosidase isolated from human placenta is different from that of recombinantly produced glucocerebrosidase by the baculovirus system.

However, upon enzymatic removal of carbohydrate, both the recombinantly produced and placental enzyme has a single major CRM form at 52 kDa.

Figure 3:
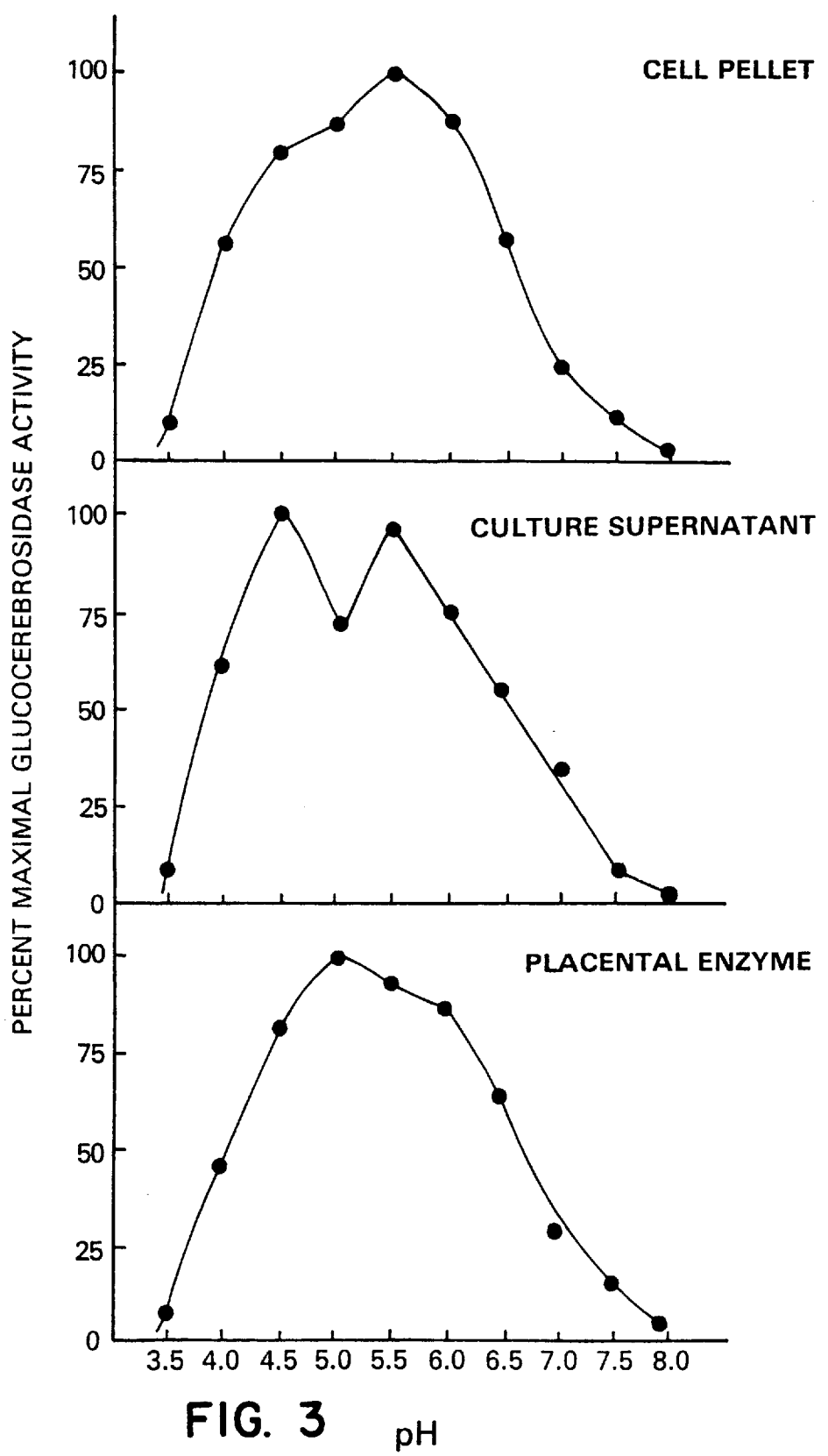
FIG. 3 shows comparative data of pH profiles of human placental glucocerebrosidase and the recombinant enzyme produced by using the baculovirus expression system. The recombinantly produced human glucocerebrosidase in both the cell pellet and the culture supernatant has a broad range of pH activity (between pH 3.5 and pH 8.0) with pH optima at approximately pH 4.5 and pH 5.5. The human placental enzyme has a broad range of pH activity (between pH 3.5 and pH 8.0) with pH optima at approximately pH 5.0 and pH 6.0.

2) The recombinant enzyme was active between pH 3.5 and pH 8.0 with pH optima at pH 4.5 and pH 5.5. The human placental enzyme was active between pH 3.5 and pH 8.0 with pH optima at pH 5.0 and pH 6.0 (See FIG. 3).

3) The recombinantly produced enzyme in the media and cell pellet have Km's of 3.3 mM and 3.6 mM. respectively. The Km for the placental enzyme is reported to be 8 mM (Basu et al, J.B.C. 259:1714, 1984).

It is clear from the above that the recombinantly produced GCS of the present invention is a qualitatively different protein than any other heretofore known entity.

Since the carbohydrate pattern of the recombinantly produced GCS of the present invention is more like that of the human liver, spleen, brain or macrophage GCS, as compared to the placental enzyme and obtained in large quantities by the expression vector of the present invention, replacement therapy of Gaucher's disease now becomes possible for treating patients afflicted with this disease. A method of treating this disease comprises administering to a subject afflicted with Gaucher's disease, therapeutic amounts of recombinant GCS of the present invention to alleviate said disease condition.

A pharmaceutical composition comprises therapeutic amounts of the GCS of the present invention and pharmaceutically acceptable carrier such as physiological saline, non-toxic sterile buffers and the like.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A pharmaceutical composition comprising a therapeutic amount of a glycosylated recombinantly-produced human glucocerebrosidase protein having an amino acid sequence given in FIG. 1 in a pharmaceutically acceptable carrier.

2. A method of treating Gaucher's disease comprising administering to a subject afflicted with said disease a therapeutic amount of a pharmaceutical composition of claim 1.

* * * * *